United States Patent [19]
Hertelendy et al.

[11] Patent Number: 6,099,853
[45] Date of Patent: Aug. 8, 2000

[54] VAGINAL SUPPOSITORY VACCINE FOR UROGENITAL INFECTIONS

[75] Inventors: Zsolt Istvan Hertelendy; Murray Weiner, both of Cincinnati, Ohio

[73] Assignee: Protein Express, Cincinnati, Ohio

[21] Appl. No.: 08/923,813

[22] Filed: Sep. 4, 1997

[51] Int. Cl.⁷ ............................ A61K 9/02; A61K 39/116
[52] U.S. Cl. ........................ 424/433; 424/436; 424/203.1
[58] Field of Search .................... 424/433, 203, 424/203.1, 257.1, 259.1, 244.1, 436

[56] References Cited

U.S. PATENT DOCUMENTS

| | | | |
|---|---|---|---|
| 3,880,991 | 4/1975 | Yolles | 425/432 |
| 4,606,919 | 8/1986 | Stojkovic et al. | 424/203.1 |
| 4,820,698 | 4/1989 | Degenhardt et al. | 514/102 |
| 4,939,284 | 7/1990 | Degenhardt | 558/142 |
| 5,057,520 | 10/1991 | Chu et al. | 514/300 |
| 5,057,523 | 10/1991 | Chu et al. | 514/312 |
| 5,270,344 | 12/1993 | Herman | 514/725 |
| 5,364,879 | 11/1994 | Herman | 514/452 |

OTHER PUBLICATIONS

Solco Basle Ltd. Brochure: SolcoUrovac, A Vaccine for the Treatment and Prophylaxis of Chronic Urinary Infections.
Robert F. Service, Medical Research—New Vaccines May Ward Off Urinary Tract Infections, *Science*, vol. 276, p. 533, Apr. 25, 1997.
David T. Uehling, et al., Decreased Immunologic Responsiveness Following Intensified Vaginal Immunization Against Urinary Tract Infection, *The Jouranl of Urology*, vol. 143, pp. 143–145, Jan. 1990.
David T. Uehling, et al., Urinary Glycosaminoglycan Levels Following Induced Cystitis in Monkeys, *The Journal of Urology*, vol. 139, pp. 1103–1105, May 1988.
Walter J. Hopkins, et al., Local and Systemic Antibody Responses Accompany Spontaneous Resolution of Experimental Cystitis in Cynomolgus Monkeys, *Infection and Immunity*, vol. 55, No. 9., pp. 1951–1956, Sep. 1987.
David T. Uehling, et al., Vaginal Immunization Against Induced Cystitis In Monkeys, *The Journal of Urology*, vol. 137, pp. 327–329, Feb. 1987.
Walter J. Hopkins, et al., In Vitro And In Vivo Adherence Of Uropathogenic *Escherichia Coli* Strains, *The Journal of Urology*, vol. 135, pp. 1319–1321, Jun. 1986.
David T. Uehling, M.D., Future Approaches to the Management of Urinary Tract Infections, *Urologic Clinics of North America*, vol. 13, No. 4, pp. 749–758, Nov. 1986.
David T. Uehling, et al., A Quantitative In Vivo Assay For Bacterial Adherence To The Urethra, *The Journal of Urology*, vol. 133, pp. 316–318, Feb. 1985.
J. Jensen, et al., Enhanced Immune Response In The Urinary Tract Of The Rat Following Vaginal Immunization, *The Journal of Urology*, vol. 132, pp. 164–166.
D.T.Uehling, et al., Immunization Against Urinary Tract Infections, *Journal d'Urologie*, vol. 91, No. 1, pp. 23–26, 1985.

H. Rüttgers, E. Grischke, Elevation of Secretary IgA Antibodies in the Urinary Tract by Immunostimulation for the Pre–Operative Treatment and Post–Operative Prevention of Urinary Tract Infections, *Urologia Internationalis*, vol. 42, No. 6, pp. 1–3, 1987.
E.M. Grischek, et al., Treatment of Bacterial Infections of the Female Urinary Tract by Immunization of the Patients, *Urologia Internationalis*, vol. 42, No. 5, pp. 1–4, 1987.
H. Rüttgers, et. al., Urinary Tract Infections in Women— Current Unsatisfactory Situation and Prospects of a New Therapeutic Concept, *Urologia Internationalis*, vol. 42, No. 5, pp. 1–6, 1987.
D. Kruze, et al., Urinary antibody response after immunisation with a vaccine against urinary tract infection, *Urological Research*, vol. 17, pp. 361–366, 1989.
Mary Crowley, 6 Ways to prevent a bladder infection . . . without giving up sex, *Glamour*. vol. 95, No. 3, p. 82, 1997.
David Uehling, Newer Techniques in the Diagnosis of Children's Urinary Tract Infections, *The Wisconsin Medical Journal*, pp. 279–281, Aug., 1965.
D. T. Uehling, et al., Antibody Production In Urinary Bladder Infection, *Investigative Urology*, vol. 6, No. 2, pp. 211–227, Sep. 1968.
David T. Uehling, et al., Enhancement of the Bladder Defense Mechanism by Immunization, *Investigative Urology*, vol. 6, No. 5, pp. 52–526, Mar. 1969.
David T. Uehling, et al., Prevention of Catheter Bacteriuria, *Wisconsin Medical Journal*, vol. 69, pp. 68–69, Jun. 1969.
D. T. Uehling, et al., Serum Antibody Effect on Induced Bladder Infection, *Investigative Urology*, vol. 8, No. 1, pp. 62–65, Jul. 1970.
D. T. Ueling, et al., Elevated Urinary Secretory IgA in Children with Urinary Tract Infection, *Pediatrics*, vol. 47, No. 1 pp. 40–46, Jan. 1970.
David T. Uehling, Urinary Immunoglobulin Excretion in Induced Urinary Infection, *Investigative Urology*, vol. 9, No. 5, pp. 408–410, Mar. 1972.
D. T. Uehling, et al., Immunoglobulin Excretion In Women With Recurrent Urinary Tract Infection, *The Journal of Urology*, vol. 109, pp. 302–303, Feb., 1973.

(List continued on next page.)

*Primary Examiner*—Mary E. Mosher
*Attorney, Agent, or Firm*—Arter & Hadden LLP

[57] ABSTRACT

This invention is directed to a suppository-based vaccine delivery system for immunizing against urogenital infectious disease in humans and a method for treating same. More particularly, this invention is directed to a suppository-based vaccine delivery system for the prophylaxis against urogenital infectious diseases, such as urinary tract infections. The suppository-based vaccine delivery system is comprised of a vaccine comprised of inactivated bacteria which originate from cultures of 8 to 14 uropathogenic bacteria strains of the species: *Escherichia coli, Klebsiella pnieumoniae, Proteus mirabilis, Proteus morganii*, and *Streptococcus faecalis*; and polyethylene glycol suppository base; wherein the suppository is adapted to be inserted into a bodily orifice of a human so as to allow the suppository to be in contact with tissue of the bodily orifice to facilitate transfer of suppository material therethrough.

28 Claims, 1 Drawing Sheet

OTHER PUBLICATIONS

David T. Uehling, et al., Secretoary Immunoglobulin–A Excretion in Cystitis Cystica, *Urology*, vol. 1, No. 4, pp. 305–306, Apr. 1973.

Calvin M. Kunin, et al., Detection of Urinary Tract Infections in 3– to 5– Year Old Girls by Mothers Using a Nitrite Indicator Strip, *Pediatrics*, vol. 57, No. 6, pp. 829–835, Jun., 1976.

David Uehling, Quantitation of Urinary Immunoglobulins by a Double Antibody Technique, *Investigtive Urology*, vol. 15, No. 1, pp. 39–41, 1977.

David T. Uehling, Effect f Immunication on Bacterial Adherence to Urothelium, *Investigative Urology*, vol. 16, No. 2, pp. 145–147, Sep. 1978.

David T. Uehling, et al., Bladder Adherence to Urothelium, *Surgical Forum*.

Calvin M. Kunin, et al. Trimethoprim Therapy for Urinary Tract Infection, *Jama*, vol. 239, No. 24, pp. 2588–2590, Jun., 1978.

David T. Uehling, The Normal Caliber of the Adult Female Urethra, *The Journal of Urology*, vol. 120, pp. 176–177, Oct., 1977.

David T. Uehling, Inhibitors of Bacterial Adherence to Urothelium, *Investigtive Urology*, vol. 18, No. 1, pp. 40–42, Jul. 1980.

Jean Jensen, et al., Resolution of Induced Urinary Tract Infection: An Animal Model to Assess Bladder Immunization, vol. 127, pp. 1220–1222, Nov., 1982.

David T. Uehling, Vaginal Immunication Against Urinary Tract Infection, *The Journal of Urology*, vol. 128, pp. 1382–1394, Dec. 1982.

David T. Uehling, Inflammatory Diseases of the Bladder, *Adult Urology*, pp. 1101–1118.

M. Litschgi, Harwegsinfektbehandlund mit SolcoUrovac, Geburtshilfe und Frauenheilkunde 47: 107–110, 1987.

Dorlan's Illustrated Medical Dictionary, 27th ed., W.B. Saunders Co., Philadelphia PA, p. 1365, 1988.

Uehling et al, Journal of Urology 157:2049–2052, 1997.

VAGINAL SUPPOSITORY VACCINE FOR UROGENITAL INFECTIONS

FIELD OF INVENTION

The present invention relates generally to a system and method for treating disease in humans, specifically a prophylactic treatment of urogenital infections in humans. More particularly, the invention relates to a suppository-based, intravaginal vaccine delivery system for prophylaxis against urinary tract infections in humans, wherein the suppository is comprised of a vaccine derived from whole or fractionated pathogenic microorganisms. Still more particularly, the present invention relates to a suppository based delivery system for prophylaxis against recurrent urinary tract infections in humans, wherein the suppository is comprised of a vaccine of whole, inactivated bacteria which originate from cultures of 4 to 20 uropathogenic bacterial strains isolated from the urine of persons suffering urinary tract infections, and which include a polyethylene glycol suppository base.

BACKGROUND OF THE INVENTION

Urinary tract infections are a major problem in medicine. Every part of the urinary tract may be affected. The most common forms of the illness are: cystitis, the urethral syndrome, pyelitis, and pyelonephritis. A tendency for recurrence and chronic progression is characteristic of urinary tract infections. The disease is ten times more common in women than men. This difference is due mainly to the fact that the particular anatomy of the female urethra favors infection by the body's own bacterial intestinal flora. The main diagnostic criterion of urinary tract infections is bacteriuria, the presence of bacteria in the properly collected urine sample (midstream urine). For bacteriuria to be considered diagnostically significant, it has to exceed a concentration of $10^5$ bacteria per milliliter of urine. bacteriuria to be considered diagnostically significant, it has to exceed a concentration of $10^5$ bacteria per milliliter of urine.

Bacteria that reach the urinary tract establish infection either through the bloodstream or by ascending from the urethra to the bladder and then up the ureter to the kidneys. Ascending infection is the most common mode and explains the more frequent occurrence in women. The position of the urethral ostium and the short urethra in women favor infection. Various bacteria originating from the fecal flora are always resident in the urethral ostium and in the distal part of the female urethra. Urinary tract infections in women is initiated when one of the Enterobacteriaceae derived from the fecal flora colonizes in the vaginal vestibule.

The most frequent and abundant constituent of the fecal flora is *Escherichia coli*, which is also frequently found in the urine as the causative organism in urinary tract infections. *Escherichia coli* is also usually found in the periurethral region. This bacterium is capable of adhering to the periurcthral epithelial cells. Bacterial adherence is the precondition for the colonization and infection of the urinary tract. Many in-vitro studies have shown that the adherence phenomenon is due to the possession of pili by *Escherichia coli* that infect the urinary tract. *Escherichia coli* bacteria are the most frequent causative agents of urinary tract infections.

The urinary tract can also be colonized by other Enterobacteria, such as Proteus and Klebsiella, and gram positive cocci such as Staphylococcus and *Streptococcus faecalis* (Enterococcus). Other bacteria such as *Pseudomonas aeruginesa* and *Haemophilus influenzae* may also invade the urinary tract. Any of the bacterial inhabitants of the intestinal tract that are eliminated in the feces may populate the urinary tracts. Further, the human urinary tract can be colonized by mycoplasma, L-forms of bacteria, Chlamydia, fungi, viruses, and protozoa.

Recurrence and chronicity are characteristic of urinary tract infections. Recurrence may be due to either relapse or reinfection. In spite of a great deal of progress in the treatment of other bacterial infections, the morbidity and mortality of urinary tract infections's remains unchanged in the last 20 to 25 years. The reasons for this are myriad and depend on the host organism and on microbial factors.

Recurrences of infections with a previously infecting organism strain are rare and may result from incorrect choice of medicine, emergence of resistance strains, insufficient treatment duration, insufficient concentration of antibacterial agents, the existence of bacterial L-forms, and survival of organisms in urinary calculi. Recurrent urinary tract infections in women are essentially all reinfections with different organisms and generally with strains having a greater capacity to adhere to the epithelial cells of the vagina and urethra. The reinfecting bacteria originate in the intestinal flora. The composition of the intestinal flora may be altered by prophylactic and therapeutic use of antibiotics and other antibacterial materials which are used in the treatment and prophylaxis of urinary tract infections. The intestinal flora frequently develop antibiotic resistance and the resistant bacteria may then cause a reinfection or primary opportunistic infection of the urinary tract. Such primary infections may be due to opportunistic germs that result from the normal, harmless flora, such as lactobaelli, being wiped out by antibiotics. Other microbes, resistant to the antibiotics, can now flourish and become pathogenic. The bacterial antibiotic resistance caused by R-plasmids is not only transferred between the same species of bacteria, but is also transmitted to almost all Enterobacteriaceae. Multiresistance is also common.

The main cause of recurrent urinary tract infections in women is an immunological defect which facilitates the adhesion of uropathogenic organisms to the periurethral region. Studies have revealed that low levels of urine secretory IgA (sIgA) in urine indicate a defective local immune response of the urinary tract and favor recurrent ascending urinary tract infections. The most important property of sIgA is that they prevent the interaction of bacterial pili with the specific receptors found on the epithelia of the urinary tract. Pili-mediated adhesiveness is an important virulence factor of the bacterial involved. For the defense against infection it is important to reduce the adhesion of the pathogens to the urothelium or to prevent the attachment of the bacteria altogether.

Normally, the host organism forms specific local antibodies against the invading bacteria and secretes these antibodies as sIgA. In patients with persisting or frequently relapsing urinary tract infections this natural mechanism of local immunological infection defense is apparently disturbed. Therefore, enhancement of immune defense is a rational means of eliminating the cause of recurrent urinary tract infections. A vaccination which stimulates the production of antibodies to a spectrum of antigens that are present in several types of *Escherichia coli* and other commonly occurring urinary bacteria is particularly appropriate.

Previously, urinary tract infections vaccines have been administered parenterally or orally and have resulted in enhanced resistance to urinary tract infections. Parenteral administration of SOLCOUROVAC®, a urinary tract infections vaccine manufactured by Solco Basel AG, Basel Switzerland and described in U.S. Pat. No. 4,606,919, the contents of which are incorporated herein in entirety, decreased post-hysterectomy urinary tract infections, reduced the frequency of infections in susceptible women, and increased sIgA. However, some patients suffered from side effects such as malaise, fever, and muscle soreness. An oral vaccine consisting of immunostimulatory fractions extracted from *Escherichia coli* strains decreased bacteriuria, septic episodes, requirements for antibiotics in spinal cord injury patients, and the incidence of recurrent urinary tract infections in adult women. As with the parenteral administration, many patients suffered from adverse reactions.

In an attempt to overcome the defects associated with parenteral and oral administrations of urinary tract infections vaccine, an intravaginal vaccine against urinary tract infections was proposed. The rationale for administering a urinary tract infections vaccine intravaginally was that there is a mucosal immune system wherein antigens are absorbed through mucosal surfaces and processed by specialized local lymphoid tissues, after which antibodies are secreted onto local mucosal surfaces. As discussed above, in the genitourinary tract, temporary or partial deficiencies in local vaginal or urinary antibodies are an important factor in the heightened susceptibility to urinary tract infections shown in some women. Immunization via the mucosal surfaces within the genitourinary tract are preferable to parental or oral routes as it has been discovered that vaccination via the intravaginal surface creates a secretory immune response in the urogenital tract.

In the past, urinary tract infections vaccines were administered vaginally in the form of a liquid vaccine. Several problems were associated with the intravaginal administration of liquid urinary tract infections vaccine. The major problem encountered was that the liquid vaccine flowed out of the vagina soon after insertion. This severely limits the amount of time that the liquid antigens are in contact with the mucosal surface of the vagina, decreasing the effectiveness of the vaccine. The antigens need sufficient contact with the vaginal mucous membrane to elicit a secretory immunoglobin response. Patients receiving the vaccination were required to lie in a supine position for an extended time after receiving the vaccine to prevent the vaccine from immediately flowing out of the vagina. However, often the vaccine still leaked out of the vagina following the period of time in the supine position, limiting the effectiveness of the vaccine.

In addition, the requirement that patients lie in a supine position for an extended time after receiving the vaccine, is a burden on the patient. Patients may receive several vaccinations over the course of treatment and the patients must spend a considerable amount of time after each vaccination immobile. Therefore, it is apparent that improvements are necessary in the prophylaxis against urogenital infectious diseases, such as urinary tract infections, and urinary tract infection vaccines.

The subject invention overcomes the above limitations and others, and teaches a suppository-based vaccine delivery system for prophylaxis against urogenital infectious diseases, such as urinary tract infections.

SUMMARY OF THE INVENTION

According to the present invention, there is provided a intravaginally administered suppository-based vaccine delivery system for prophylaxis against urogenital infectious diseases, such as urinary tract infections.

Further according to the present invention, there is provided a suppository-based vaccine delivery system for the prophylaxis against urogenital infectious diseases, such as urinary tract infections wherein the vaccine is in contact with the vaginal mucous membrane for a sufficient period of time to enhance the immune response.

Still further according to the present invention, there is provided a suppository-based vaccine delivery system for the prophylaxis against urogenital infectious diseases, such as urinary tract infections, wherein the vaccine is easily administered, does not require the patient to lie in a supine position for an extended period of time after receiving the vaccination, and is suitably administered by the patient for primary and routine booster requirements.

Still further according to the present invention, there is provided a suppository-based vaccine delivery system for prophylaxis against urogenital infectious diseases, such as urinary tract infections in humans, said suppository comprising: a vaccine comprised of inactivated bacteria which originate from cultures of 8 to 14 uropathogenic bacteria strains isolated from the urine of persons suffering from a urinary tract infection of the species: *Escherichia coli, Klebsiella pneumoniae, Proteus mirabilis, Proteus morganii,* and *Streptococcus faecalis,* and are present in an amount of about 50 million to about 5 billion germs of each strain per suppository, wherein one-half to three-quarters of the strains used belong to *Escherichia coli* species; and polyethylene glycol suppository base; wherein the suppository is adapted to be inserted vaginally so as to allow the suppository to be in contact with vaginal mucous membrane to facilitate transfer of suppository material therethrough.

An advantage of the present invention is the provision of a suppository-based vaccine delivery system for the prophylaxis against urogenital infectious diseases, such as urinary tract infections, wherein the vaccine is in contact with the vaginal mucous membrane for a sufficient period of time to enhance the immune response.

Another advantage of the present invention is the provision of a suppository-based vaccine delivery system for the prophylaxis against urogenital infectious diseases, such as urinary tract infections, wherein the vaccine is easily administered, and does not require the patient to be in a supine position for an extended period of time after receiving the vaccination.

Another advantage of the present invention is the provision of a suppository-based vaccine delivery system wherein the vaccine is suitably administered by the patient.

Another advantage of the present invention is the provision of a suppository-based vaccine delivery system wherein the administration of the vaccine is relatively painless.

Yet another advantage of the present invention is the provision of a suppository-based vaccine delivery system wherein sIgA—specific stimulation from mucosal vaccination allows immune responses to specifically keep bacterial colonization from occurring, instead of fighting the infection once it has colonized.

Yet another advantage of the present invention is the provision of a suppository-based vaccine delivery system wherein the patient may self-administer booster vaccinations periodically.

Still other advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENT

Figure 1:
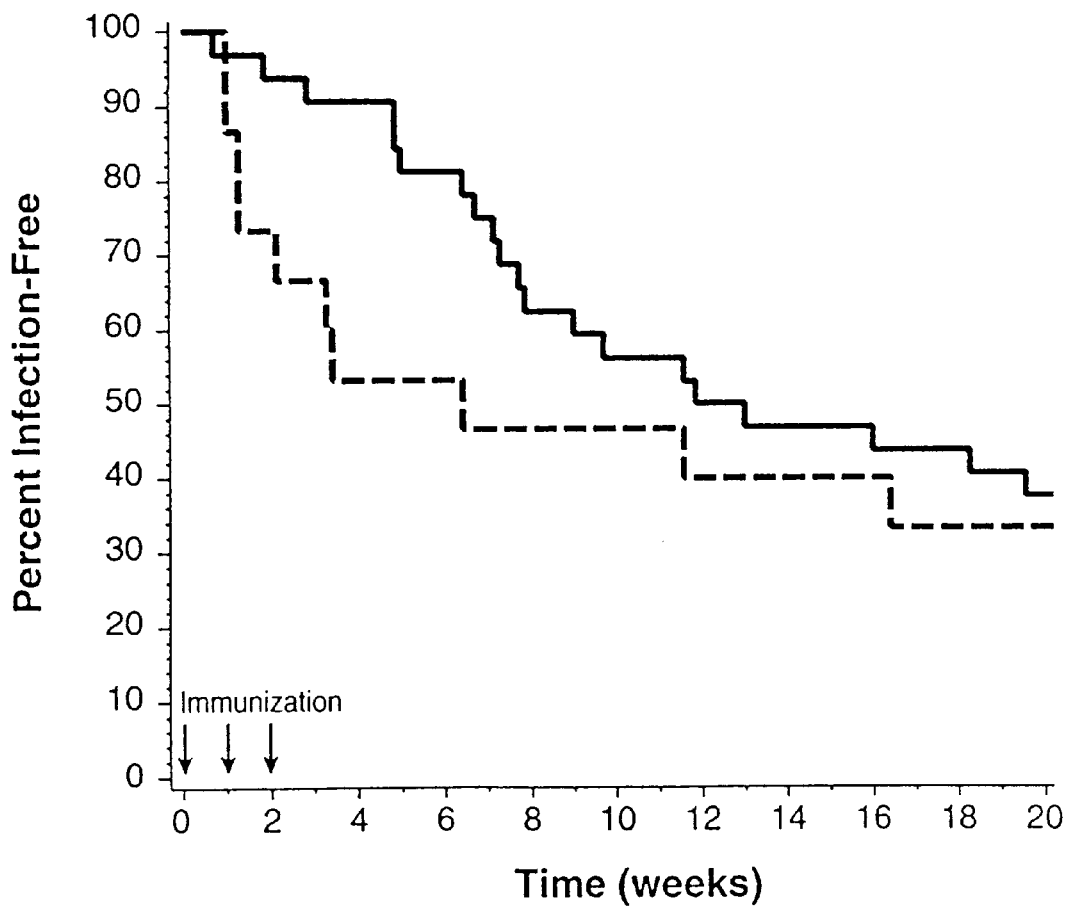
FIG. 1 is a graph illustrating the percentage of patients remaining infection free during the course of the testing.

This invention is directed to a suppository-based vaccine delivery system for immunizing against infectious disease in humans and a method for treating same. More particularly, this invention is directed to a suppository-based vaccine delivery system for the prophylaxis against urogenital infectious diseases, such as urinary tract infections. The suppository-based vaccine delivery system is comprised of a vaccine comprised of inactivated bacteria which originate from cultures of 8 to 14 uropathogenic bacteria strains of the species: *Escherichia coli, Klebsiella pneumoniae, Proteus mirabilis, Proteus morganii*, and *Streptococcus faecalis*; and polyethylene glycol suppository base; wherein the suppository is adapted to be inserted into a bodily orifice of a human so as to allow the suppository to be in contact with tissue of the bodily orifice to facilitate transfer of suppository material therethrough.

The suppository is comprised of a vaccine comprised of inactivated bacteria which originate from cultures of 8 to 14 uropathogenic bacteria strains of the species: *Escherichia coli, Klebsiella pneumoniae, Proteus mirabilis, Proteus morganii*, and *Streptococcus faecalis*. The inactivated bacteria are present in an amount of about 50 million to about 5 billion germs of each strain per suppository and one half to three-quarters of the strains used belong to the *Escherichia coli* species. Preferably, the inactive bacteria originate from 6 strains of the species *Escherichia coli* and 1 strain each of *Klebsiella pneumoniae, Proteus mirabilis, Proteus morganii*, and *Streptococcus faecalis*. In a preferred embodiment, the inactive bacteria are present in the total amount of about $1 \times 10^9$ to about $1 \times 10^{10}$ germs.

The suppository is comprised of a vaccine which is prepared according to the method described in U.S. Pat. No. 4,606,919, which is incorporated by reference in its entirety. The vaccine is prepared by culturing, by themselves on a suitable nutrient medium, each of the above mentioned 8 to 14 uropathogenic bacteria strains which have been isolated from the urine of persons suffering from an infection of the urinary tract and, when culturing is concluded, removing the particular biological material formed and inactivating it by known methods, mixing amounts of the inactivated bacteria obtained from the individual strains with one another and diluting the mixture with an amount of a sterile isotonic solution such that about 50 million to 5 billion germs of each strain are present per suppository.

Urine samples (mid-stream urine) were first isolated from persons suffering from a urinary tract infection and inoculated immediately onto a MacConkey agar; after the inoculation, the agar plates were incubated at 37° C. for 16 to 18 hours and the colonies formed were then isolated and identified by determination of their biochemical and biological properties.

The colonies identified in this manner were allowed to grow further on agar plates at 37° C. for 24 hours and were then suspended in physiological saline solution, tested for purity by means of Gram staining and freeze-dried.

To prepare the vaccines, the strains were cultured individually on a solid or liquid nutrient medium; a solid nutrient medium is preferably used, for example nutrient agar such as Nutrient Agar Difco. The medium is sterilized at 121° C. for 15 minutes and it has a pH of about 7.2.

Roux bottles are used for large-scale preparation, and Petri dishes are used for preparation in the laboratory. Inoculation is carried out with inoculum material, a few milliliters of which are uniformly distributed over the entire surface. The Roux bottles are closed with cottonwool plugs and the medium is stored with the inoculated surface at the bottom. The inoculated cultures are incubated at 37° C. for 24 hours.

The bacterial lawns are rinsed off with the required amount (depending on the density of growth of the culture in the vessel) of phosphate buffer/saline solution with gentle swirling, without damaging the agar surface.

A smear is obtained from each bottle or each Petri dish, stained by the Gram method and tested for purity. Bottles or Petri dishes which appear to be contaminated are discarded. Suspensions which originate from one strain and one harvest are poured together through a sterile nylon gauze.

Inactivation, like the culture itself, takes place individually for each strain. It can be carried out by heating at a temperature of about 55° C. to about 60° C. for about one hour, by treatment with formaldehyde solution or by irradiation with γ-rays. Because of its simplicity, inactivation by heating is preferred. The amounts obtained by culture are combined and inactivated in a waterbath at 60° C. for one hour, and phenol is added after the inactivation.

The contents of the stock container (inactivated suspensions originating from one strain) are centrifuged at 3,000 rpm for 1 hour in a cooled centrifuge, the supernatant liquid is removed and the bacterial sediment is suspended in saline solution containing 0.01% of thimerosal.

The suppository of the present invention is comprised of any suitable polyethylene glycol suppository base known in the art. More particularly, the polyethylene glycol suppository base is comprised of polyethylene glycol and polysorbate. Preferably, the polyethylene glycol suppository base is comprised of about 98% by weight polyethylene glycol and about 2% by weight polysorbate. Preferably, the polyethylene glycol has an average molecular weight of about 3000 to 5000. In a more preferred embodiment, the polyethylene glycol suppository base is comprised of about 39% by weight of polyethylene glycol having a molecular weight of 8000 and 59% by weight of polyethylene glycol having a molecular weight of 400. A suitable commercially available polyethylene glycol suppository base is POLYBASE, manufactured by Paddock Laboratories, Inc.

The polyethylene glycol suppository base is present in the suppository-based vaccine delivery system in any suitable amount so as to allow the vaccine to be in contact with the vaginal mucous membrane for a sufficient period of time to enhance the immune response. Preferably, the polyethylene glycol suppository base comprises from about 80% to 95% by weight of the suppository. The polyethylene glycol suppository base confers a degree of miscibleness with the mucous membrane surfaces of the vagina, wherein suspended particles of the vaccine are in contact with such mucous membrane surfaces for a sufficient amount of time to elicit a secretory immunoglobin response. The polyethylene glycol suppository base has an adjuvant effect which enhances the immune response by allowing the vaccine to facilitate contact time with the vaginal mucous membranes, serving as a depot that slowly releases antigen, and by localizing and delivering antigens to immunocompetent cells. The polyethylene glycol suppository base further functions as a structural necessity which keeps the suppository in its molded form.

The suppository is inserted into a laminate suppository shell which forms a molded shape. The suppository is stored in the shell until used. The laminate suppository shell is any shell known in the art suitable for packaging of the suppository. The suppository shell must be able to withstand temperatures of 60° C. used in manufacturing the suppositories and temperatures of 4° C. for long-term storage without compromising the integrity of the mold or reacting with the suppository in an unfavorable manner. Preferably, the laminate suppository shell is a polyvinyl chloride-polyethylene laminate suppository shell. A suitable commercially available laminate suppository shell is a polyvinyl chloride-polyethylene laminate suppository shell manufactured by Paddock Laboratories, Inc.

The suppository-based vaccine system suitably further comprises depolarized gelatin. The depolarized gelatin is any suitable depolarized gelatin known in the art. Example of suitable depolarized gelatin materials include, but are not limited to, Type A or B gelatin from bovine or porcine collagen. Preferably, the depolarized gelatin is Type A gelatin. The depolarized gelatin serves to protect components during lyophilization.

The depolarized gelatin is present in the suppository in any suitable amount. More particularly, the suppository is comprised of from about 0.01% to about 0.02% by weight depolarized gelatin.

The suppository-based vaccine system suitably further comprises thimerosal. The thimerosal is antimicrobial preservative. A suitable commercially available thimerosal is available from Sigma Chemical Co. The thimerosal is present in the suppository in any suitable amount. More particularly, the suppository is comprised of from about 0.0005% to about 0.005% by weight thimerosal.

The suppository-based vaccine delivery system of the present invention is prepared under an aseptically sterile laminar flowhood. The polyethylene glycol suppository base is heated to a temperature of about 80° C. such that the polyethylene glycol becomes liquefied. The polyethylene glycol suppository base is heated for about 1 hour. The vaccine comprised of 8 to 14 strains of inactivated lyophilized uropathogenic bacteria is placed in a flask. A portion of the liquid suppository base is cooled to 60° C. and poured into individual flasks containing the vaccine. The vaccine and the liquid suppository base are stirred for about 10 minutes at a temperature of about 60° C. forming a homogeneous suspension comprised of the suppository base and the vaccine. The suspension comprised of the suppository base and the vaccine is placed into individual laminate suppository shells. An additional amount of liquid suppository base is added to the flask which contains residue of vaccine. The suppository base and the vaccine are stirred for about 1 minute at a temperature of 60° C. to form a homogeneous suspension. This suspension is added to the lambaste suppository shell. Pure liquid suppository base is added to the top of the laminate suppository shell until the shell is filled. The suppository is cooled at a temperature of about 24° C. allowing the suppository base to harden. This method ensures that the active vaccine materials are located in the bottom 67% of the suppository where it is protected from the cracking or flaking that may occur in the tip of the suppository when shells are opened for use.

The present invention is further exemplified in the following example. The example illustrates the effectiveness of the suppository-based vaccine delivery system of the present invention. It is understood that the example is only illustrative of preferred embodiments according to the present invention wherein the claims set forth the scope of the present invention.

EXAMPLE

A suppository-based vaccine delivery system comprised of a vaccine comprised of inactivated bacteria which originate from cultures of 8 to 14 uropathogenic bacteria strains isolated from the urine of persons suffering from a urinary tract infection of the species: *Escherichia coli, Klebsiella pneunioniae, Proteus mirabilis, Proteus morganii*, and *Streptococcus faecalis*, and are present in an amount of about 50 million to about 5 billion germs of each strain per suppository, wherein one-half to three-quarters of the strains used belong to *Escherichia coli* species; and polyethylene glycol suppository base; was prepared.

POLYBASE, a polyethylene glycol suppository base manufactured by Paddock Laboratories, Inc., was heated to a temperature of 80° C. for about one hour to liquefy the suppository base. Lyophilized SOLCOUROVAC® vaccine manufactured by Solco Basel AG, was aseptically placed in a sterile Erlenmeyer flask, enough to manufacture 50 suppositories. Each suppository will contain from about $1 \times 10^9$ to about $1 \times 10^{10}$ germs. The liquid suppository base was cooled to about 60° C. and approximately 100 ml of liquid suppository base was poured into the individual flasks containing the vaccine. A sterile magnetic stir bar was placed in the flask, and the vaccine and suppository base were stirred for about 10 minutes at approximately 60° C. in a temperature controlled water bath to form a homogeneous suspension. The suspension comprised of the suppository base and the vaccine was placed into individual polyvinyl chloride-polyethylene laminate suppository shell using a sterile pipette. Approximately 2.0 ml of the suspension was placed into each shell.

Approximately 25 ml of liquid suppository base is added to the flask which contained residue of the vaccine. The suppository base and the vaccine were stirred for about 1 minute at a temperature of about 60° C. to form a homogeneous suspension. Approximately 0.5 ml of this suspension was added to each shell. Pure liquid suppository base was added to each shell to fill the shell. The suppository base was cooled at a temperature of about 24° C. for about 30 minutes to harden the suppository base. The suppositories were then stored at 4° C.

Ninety one women patients, aged 18 to 82, participated in the testing of the suppository. The patients all had more than two urinary tract infections during the last year and all had an evaluation consisting of excretory urography or renal ultrasound and cystoscopy. Complete blood count, blood chemistry studies, urinalysis and culture, and speculum vaginal examination were performed on the patients prior to testing the suppository. The patients were counselled against becoming pregnant during the testing and had to have negative urine pregnancy test prior to testing.

The 91 patients were divided into three treatment groups. Group 1 received suppositories containing about $1 \times 10^9$ germs per suppository. Group 2 received suppositories containing about $2 \times 10^9$ germs per suppository. Group 3 received suppositories which did not contain the vaccine. The three groups of patients did not differ in mean age, hysterectomy status, sexual activity, or being on antibiotic prophylaxis during weeks 0–4.

The suppositories were administered three times at weekly intervals to each patient. The suppositories were administered vaginally. For vaginal suppository placement, the patients were placed in a supine position and the suppository was placed in the high vagina. The patients remained in the supine position for approximately 15 minutes. All patients were seen 4 weeks after the first treatment, and then at 4 week intervals through week 20. Serum, urine, and vaginal irrigates were collected at each visit. Vaginal cultures were done when abnormal vaginal secretions or symptoms developed during the testing.

Of the 91 patients, 44 who were on antibiotic prophylaxis at the outset of the testing continued taking antibiotics until 2 weeks after the third suppository installation. The remaining 47 were off prophylaxis regimens throughout the testing.

Patient characteristics were statistically compared with Fisher's two-tailed exact test and Kruskal-Wallis one way ANOVA. Times until first reinfection were compared with the log rank test. Such tests are fully explained in SAS/STAT Software, Changes and Enhancements, Ed. 6.07, Cary, SAS Institute, Inc., p. 620, 1993. Most infections were documented by urine culture and sensitivity, and treated for 3 days with full doses of conventional antibiotics. Episodes of typical bladder irritative symptoms which responded promptly to antibiotics available at home, but not verified by urine culture, were also counted as recurring infections and analyzed in the same manner. Changes in antibody levels during the course were compared by repeated measures ANOVA for unbalanced data.

No patients discontinued treatment for adverse reactions. One patient complained of a light-headed episode after returning home from the first vaccine, but received the second and third vaccination uneventfully and on schedule. Three other patients reported minor vaginal irritation following suppository insertions but were able to complete the three-suppository regimen without interruption. There were no other reports of episodes of heavy vaginal discharge, interference with sexual intercourse, or signs and symptoms of bacterial vaginosis.

Initial analysis of all 91 patients did not show different clinical courses between placebo and treated groups. This lack of treatment effect was due to the fact that both placebo- and vaccine-treated patients on antibiotic prophylaxis for the first 4 weeks of the study were experiencing fewer urinary tract infections. When examining the reinfection times of the 47 women off prophylaxis from week 0, the treated group experienced a significant initial delay in the time until first reinfection. There was no significant difference in the time until first infection for the low-dose and high dose groups, so these data were combined in the analysis for vaccine efficacy. The results showed that the number of patients not experiencing infection through 8 weeks was significantly greater in vaccine-treated than placebo-treated groups. In addition, the mean time until first infection was delayed from 8.7 weeks to 13 weeks in immunized patients. FIG. 1 is a graph illustrating the percentage of patients remaining infection free during the testing. Those patients in Group 1 are represented by the dotted line. The patients in Groups 2 and 3 are represented by the solid line.

The suppository-based vaccine delivery system according to the present invention allows the vaccine to be in contact with the vaginal mucous membrane for a sufficient period of time to enhance the immune response. Further, the suppository-based vaccine delivery system according to the present invention is easily administered, does not require the patient to lie in a supine position for an extended period of time after receiving the vaccination, is suitably administered by the patient, is painless, is amenable to routine urinary tract infections booster vaccination, and allows a favorable method of antigen delivery to immunocompetent cells through the mucosa.

While various embodiments of a suppository-based vaccine delivery system for treating urinary tract infections and a method for treating urinary tract infections in humans have been disclosed, it should be understood that modifications and adaptations thereof will occur to persons skilled in the art. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

Having thus described the invention, it is now claimed:

1. A suppository-based vaccine delivery system for enhancing resistance to urogenital disease in humans, said suppository comprising:
   (a) a vaccine comprised of inactivated bacteria which originate from cultures of 8 to 14 uropathogenic bacteria strains of the species: *Escherichia coli, Klebsiella pneumoniae, Proteus mirabilis, Proteus morganii,* and *Streptococcus faecalis,* and are present in an amount of about 50 million to about 5 billion germs of each strain per milliliter, wherein one-half to three-quarters of the strains used belong to *Escherichia coli* species; and
   (b) polyethylene glycol suppository base,
   wherein the suppository is adapted to be inserted into a bodily orifice of a human so as to allow the suppository to be in contact with tissue of the bodily orifice to facilitate transfer of suppository material therethrough.

2. A suppository-based vaccine delivery system for enhancing resistance to urinary tract infections in humans, said suppository comprising:
   (a) a vaccine comprised of inactivated bacteria which originate from cultures of 8 to 14 uropathogenic bacteria strains isolated from the urine of persons suffering from a urinary tract infection of the species: *Escherichia coli, Klebsiella pneumnoniae, Proteus mirabilis, Proteus morganii,* and *Streptococcus faecalis,* and are present in an amount of about 50 million to about 5 billion germs of each strain per suppository, wherein one-half to three-quarters of the strains used belong to *Escherichia coli* species; and
   (b) polyethylene glycol suppository base,
   wherein the suppository is adapted to be inserted vaginally so as to allow the suppository to be in contact with vaginal mucous membrane to facilitate transfer of suppository material therethrough.

3. The suppository-based vaccine delivery system of claim 2 wherein the inactive bacteria originate from 6 strains of the species *Escherichia coli* and 1 strain each of *Klebsiella pneumoniae, Proteus mirabilis, Proteus morganii,* and *Streptococcus faecalis.*

4. The suppository-based vaccine delivery system of claim 2 wherein the inactive bacteria are present in the total amount of about $1 \times 10^9$ to about $1 \times 10^{10}$ germs.

5. The suppository-based vaccine delivery system of claim 2 wherein the polyethylene glycol suppository base is comprised of polyethylene glycol and polysorbate.

6. The suppository-based vaccine delivery system of claim 5 wherein the polyethylene glycol suppository base is comprised of about 98% by weight polyethylene glycol and about 2% by weight polysorbate.

7. The suppository-based vaccine delivery system of claim 5 wherein the polyethylene glycol has an average molecular weight of about 3000 to about 5000.

8. The suppository-based vaccine delivery system of claim 2 wherein the polyethylene glycol suppository base comprises from about 80% to about 95% by weight of the suppository.

9. The suppository-based vaccine delivery system of claim 2 wherein the suppository is further comprised of depolarized gelatin.

10. The suppository-based vaccine delivery system of claim 9 wherein the depolarized gelatin is selected from the group consisting of type A gelatin from bovine collagen, type A gelatin from porcine collagen, type B gelatin from bovine collagen, and type B gelatin from porcine collagen.

11. The suppository-based vaccine delivery system of claim 9 wherein the suppository is comprised of about 0.01% to about 0.02% by weight of depolarized gelatin.

12. The suppository-based vaccine delivery system of claim 2 wherein the suppository is further comprised of thimerosal.

13. The suppository-based vaccine delivery system of claim 12 wherein the suppository is comprised of about 0.0005% to about 0.005% by weight of thimerosal.

14. A suppository-based vaccine delivery system for enhancing resistance to urinary tract infections in humans, said suppository comprising:
(a) a vaccine comprised of inactivated bacteria which originate from cultures of 8 to 14 uropathogenic bacteria strains isolated from the urine of persons suffering from a urinary tract infection of the species: *Escherichia coli, Klebsiella pneumoniae, Proteus mirabilis, Proteus morganii*, and *Streptococcus faecalis*, and are present in an amount of about 50 million to about 5 billion germs of each strain per suppository, wherein one-half to three-quarters of the strains used belong to *Escherichia coli* species, wherein the inactive bacteria originate from 6 strains of the species *Escherichia coli* and 1 strain each of *Klebsiella pneumoniae, Proteus mirabilis, Proteus morganii*, and *Streptococcus faecalis*, and wherein the inactive bacteria are present in the total amount of about $1 \times 10^9$ to about $1 \times 10^{10}$ germs; and
(b) polyethylene glycol suppository base,
wherein the polyethylene glycol suppository base is comprised of about 98% by weight polyethylene glycol and about 2% by weight polysorbate, wherein the polyethylene glycol has an average molecular weight of about 3000 to about 5000, and wherein the polyethylene glycol suppository base comprises from about 80% to about 95% by weight of the suppository; wherein the suppository is adapted to be inserted vaginally so as to allow the suppository to be in contact with vaginal mucous membrane to facilitate transfer of suppository material therethrough.

15. The suppository-based vaccine delivery system of claim 14 wherein the suppository is further comprised of depolarized gelatin and thimerosal, wherein the depolarized gelatin is selected from the group consisting of type A gelatin from bovine collagen, type A gelatin from porcine collagen, type B gelatin from bovine collagen, and type B gelatin from porcine collagen, wherein the suppository is comprised of about 0.01% to about 0.02% by weight of depolarized gelatin, and wherein the suppository is comprised of about 0.0005% to about 0.005% by weight of thimerosal.

16. A method for enhancing resistance to urogenital disease in humans, said method comprising the steps of:
(a) inserting a suppository-based vaccine delivery system into a bodily orifice of a human, wherein said suppository is comprised of a vaccine comprised of inactivated bacteria which originate from cultures of 8 to 14 uropathogenic bacteria strains of the species: *Escherichia coli, Klebsiella pneumoniae, Proteus mirabilis, Proteus inorganii*, and *Streptococcus faecalis*, and are present in an amount of about 50 million to about 5 billion germs of each strain per suppository, wherein one-half to three-quarters of the strains used belong to *Escherichia coli* species; and polyethylene glycol suppository base; and
(b) contacting the suppository with tissue of the bodily orifice to facilitate transfer of suppository material therethrough and induce an immune response in the human.

17. A method of enhancing resistance to urinary tract infections in humans, said method comprising the steps of:
(a) inserting a suppository-based vaccine delivery system into a vagina of a human, wherein said suppository is comprised of a vaccine comprised of inactivated bacteria which originate from cultures of 8 to 14 uropathogenic bacteria strains of the species: *Escherichia coli, Klebsiella pineumoniae, Proteus mirabilis, Proteus morganii*, and *Streptococcus faecalis*, and are present in an amount of about 50 million to about 5 billion germs of each strain per suppository, wherein one-half to three-quarters of the strains used belong to *Escherichia coli* species; and polyethylene glycol suppository base; and
(b) contacting the suppository with vaginal mucous membrane to facilitate transfer of suppository material therethrough and induce an immune response in the human.

18. The method of claim 17 wherein the inactive bacteria originate from 6 strains of the species *Escherichia coli* and 1 strain each of *Klebsiella pneumnoniae, Proteus mirabilis, Proteus morganii*, and *Streptococcus faecalis*.

19. The method of claim 17 wherein the inactive bacteria are present in the total amount of about $1 \times 10^9$ to about $1 \times 10^{10}$ germs.

20. The method of claim 17 wherein the polyethylene glycol suppository base is comprised of polyethylene glycol and polysorbate.

21. The method of claim 20 wherein the polyethylene glycol suppository base is comprised of about 98% by weight polyethylene glycol and about 2% by weight polysorbate.

22. The method of claim 20 wherein the polyethylene glycol has an average molecular weight of about 3000 to about 5000.

23. The method of claim 17 wherein the polyethylene glycol suppository base comprises from about 80% to about 95% by weight of the suppository.

24. The method of claim 17 wherein the suppository is further comprised of depolarized gelatin.

25. The method of claim 24 wherein the depolarized gelatin is selected from the group consisting of type A gelatin from bovine collagen, type A gelatin from porcine collagen, type B gelatin from bovine collagen, and type B gelatin from porcine collagen.

26. The method of claim 24 wherein the suppository is comprised of about 0.01% to about 0.02% by weight of depolarized gelatin.

27. The method of claim 17 wherein the suppository is further comprised of thimerosal.

28. The method of claim 27 wherein the suppository is comprised of about 0.0005% to about 0.005% by weight of thimerosal.

* * * * *